US011952564B2

(12) United States Patent
Xia et al.

(10) Patent No.: US 11,952,564 B2
(45) Date of Patent: Apr. 9, 2024

(54) CLOSED CELL CULTURING AND HARVESTING SYSTEM

(71) Applicant: Shanghai Longevity Co., Ltd., Shanghai (CN)

(72) Inventors: Tian Xia, Shanghai (CN); Ke Ma, Shanghai (CN)

(73) Assignee: Shanghai Longevity Co., Ltd., Shanghai (CN)

(*) Notice: Subject to any disclaimer, the term of this patent is extended or adjusted under 35 U.S.C. 154(b) by 42 days.

(21) Appl. No.: 17/899,241

(22) Filed: Aug. 30, 2022

(65) Prior Publication Data

US 2023/0022474 A1    Jan. 26, 2023

Related U.S. Application Data

(63) Continuation of application No. 17/459,156, filed on Aug. 27, 2021, now Pat. No. 11,459,536.

(30) Foreign Application Priority Data

Jul. 26, 2021    (WO) ................ PCT/CN2021/108372

(51) Int. Cl.
*C12M 1/26*    (2006.01)
*C12M 1/00*    (2006.01)
(Continued)

(52) U.S. Cl.
CPC ............ *C12M 33/14* (2013.01); *C12M 23/22* (2013.01); *C12M 23/38* (2013.01); *C12M 27/10* (2013.01); *C12M 41/42* (2013.01)

(58) Field of Classification Search
CPC ...... C12M 33/14; C12M 23/22; C12M 23/38; C12M 27/10; C12M 41/42
(Continued)

(56) References Cited

U.S. PATENT DOCUMENTS 5,057,429 A    10/1991    Watanabe et al.
5,270,192 A    12/1993    Li et al.
(Continued)

FOREIGN PATENT DOCUMENTS

WO    2018082552 A1    5/2018
WO    2021074255 A1    4/2021

OTHER PUBLICATIONS

International Search Report and Written Opinion of the International Searching Authority for PCT/CN2022/108034 dated Oct. 27, 2022 (10 pages).

*Primary Examiner* — Michael L Hobbs
*Assistant Examiner* — Lenora A Abel
(74) *Attorney, Agent, or Firm* — Sheppard Mullin Richter & Hampton LLP

(57) ABSTRACT

A bioreactor includes a base and a lid. The base includes two opposing curved or convoluted surfaces, two opposing flat surfaces, a window disposed on one of the flat surfaces, the window having a higher degree of transparency compared to other portions of the base, wherein images or videos of cells are captured through the window by non-invasive ISM device, and a rounded bottom. The lid is attachable to the base. The lid includes a shaft and a semipermeable membrane attached to the shaft, the semipermeable membrane being permeable to oxygen but impermeable to viruses and bacteria. The PAT-based online analysis directs the adaptive manipulations of bioreactor towards efficient, automated, and GMP-compliant clinical protocols of cell culture.

20 Claims, 10 Drawing Sheets

(51) Int. Cl.
    *C12M 1/34*     (2006.01)
    *C12M 3/04*     (2006.01)

(58) Field of Classification Search
    USPC ........................................................ 435/297.1
    See application file for complete search history.

(56) References Cited

U.S. PATENT DOCUMENTS

| | | |
|---|---|---|
| 6,562,616 B1 | 5/2003 | Toner et al. |
| 7,897,054 B2 | 3/2011 | Dolecek |
| 9,050,609 B2 | 6/2015 | Merino |
| 2002/0146817 A1 | 10/2002 | Cannon et al. |
| 2006/0001865 A1 | 1/2006 | Bellalou et al. |
| 2009/0148941 A1 | 6/2009 | Florez et al. |
| 2020/0032185 A1 | 1/2020 | Amer et al. |
| 2020/0165558 A1 | 5/2020 | Shevitz |

CLOSED CELL CULTURING AND HARVESTING SYSTEM

CROSS REFERENCE TO RELATED APPLICATIONS

This application is a continuation of U.S. application Ser. No. 17/459,156, filed Aug. 27, 2021, which claims priority to International Application Number PCT/CN2021/108372, filed Jul. 26, 2021, the content of each of which is incorporated by reference in its entirety into the present disclosure.

BACKGROUND

Some complex diseases such as cancer do not respond to classical pharmaceutical or biopharmaceutical product-based treatments. Cancer is a leading cause of deaths worldwide, accounting for nearly 10 million deaths in 2020. To mitigate the toll caused by cancer and other such diseases, the cross-section of oncology and vaccinology has realized advancements that include genetically engineering cells to target a particular pathogen in an adaptive immune response, a process also known as immunotherapy. This particular paradigm of targeting the immune system directly rather than the cancer cells themselves is manifested in the nascence of chimeric antigen receptor (CAR)- and T-cell receptor (TCR)-engineering techniques. Recent FDA approvals for CAR T-cell therapies, one for treatment of children with acute lymphoblastic leukemia (ALL) and another for adults with advanced lymphomas, testify to the rapid advancements in this field. In an exemplary scenario of a cancer patient, cells involved in an immune response, such as T cells or B cells, may be extracted from that patient and engineered, for example, using transduction, to express a receptor protein that specifically binds to an antigen expressed by the particular pathogen. However, after engineering the cells, the cells cannot simply be implanted back into the patient because a concentration of the cells is not nearly enough to have an impact in attacking the particular pathogen in vivo. Rather, the cells need to be grown and proliferated to reach an expansion of millions of such cells for a single therapy by many orders of magnitude prior to implanting them back into the patient. Therefore, a bioreactor that effectively and efficiently cultures and harvests cells can help fully realize the potential of current cellular technologies such as CAR and TCR T-cell therapies by establishing clinical-scale production platforms and culture modalities that maintain quality and efficacy of expansively generating genetically engineered cells. Applications of such bioreactors are not limited to cancer or disease therapeutics but may also be used in any cell culture protocols, such as Monocyte-derived Dendritic cells (Mo-DC) or mesenchymal stem or stromal cells for tissue regeneration or graft-versus-host disease therapy. The manufacturing of such bioreactors may promote T cell culture towards automation, analytical process control and complete closed system, offering a massive breakthrough for faster, easier and cheaper protocols of specific cultivation mode.

SUMMARY

Described herein, in some embodiments, is a bioreactor. The bioreactor comprises a base and a lid. The base comprises two opposing curved or convoluted surfaces, two opposing flat surfaces, a window disposed on one of the flat surfaces, the window having a higher degree of transparency compared to other portions of the base, wherein images or videos of cells are captured through the window, and a rounded, conical, or semi-conical bottom. The lid is attachable or attached to the base. The lid comprises a shaft, column, pole, stick, rod, or stem (hereinafter "shaft") and a semipermeable membrane such as polytetrafluoroethylene (PTFE), attached to the shaft. The semipermeable membrane may be gas-permeable or permeable to oxygen but impermeable to viruses and bacteria.

In some embodiments, the lid further comprises a connector disposed at a distal end of the bioreactor and attachable to an external device.

In some embodiments, the connector comprises a male Luer interface configured to mate with a female Luer interface of the external device, the external device comprising a sensor probe device, a stirring device, a liquid handling device, a cell retention device, a harvesting device, or a downstream bioreactor.

In some embodiments, the semipermeable membrane is disposed closer to the distal end of the bioreactor compared to the rounded bottom.

In some embodiments, the base further comprises a circular periphery positioned at a first, or proximal, end of the bioreactor relative to the two opposing curved or convoluted surfaces and the two opposing flat surfaces.

In some embodiments, the lid comprises a shell, shell-like portion, outer segment, covering, casing, or exterior, that fits over the circular periphery of the base. The shell possesses or comprises an array of radially scattered air holes to ensure continuous air flow.

In some embodiments, the rounded bottom is disposed at a second, or a distal, end of the bioreactor.

In some embodiments, the shaft comprises a channel through which liquids are injected into or extracted from the base.

Described herein, in some embodiments, is an assembly. The assembly comprises a bioreactor configured to culture cells. The bioreactor comprises a base and a lid. The base comprises two opposing curved or convoluted surfaces, two opposing flat surfaces, a window disposed on one of the flat surfaces, the window having a higher degree of transparency compared to other portions of the base, wherein images or videos of cells are captured through the window, and a rounded bottom. The lid may comprise a connector attachable to an external device. The assembly further comprises a rotatable rack upon which the bioreactor is attached or embedded.

In some embodiments, the assembly further comprises a motor system positioned underneath the rotatable rack, the motor system controlling a continuous mechanical rotation of the rotatable rack by rotating the rotatable rack from an upright orientation to a horizontal orientation at which cells sink and localize to a bottom horizontal flat surface so as to acquire an image or video through the window of the bioreactor.

In some embodiments, the assembly further comprises a platform positioned underneath the motor system, the platform comprising a gap, wherein an in situ microscopy (ISM) device as a non-invasive monitoring sensor is positioned within the gap and directly underneath the window when the rotatable rack is in the horizontal orientation.

In some embodiments, the rotatable rack is responsively configured to rotate to a precise angle with a specific speed based on a resolution of an image captured by the ISM device, a density of the cells within the window captured by the ISM device, or a morphology of the cells captured within the window.

In some embodiments, the motor system controls a rocking cycle of the bioreactor based on a density of the cells captured within the window by the ISM device, or a morphology of the cells captured within the window, the rocking cycle comprising two combined parameters of angle and speed associated with a shaking, a vibration, or a vortex of the bioreactor.

In some embodiments, the external device comprises a sensor probe, a liquid handling, a cell retention device, or a stirring component, and an operation of the external device is controlled based on a density of the cells captured by the ISM device within the window, or a morphology of the cells captured within the window.

In some embodiments, the ISM device translates, for example, within a region of the gap, to capture images of additional bioreactors fixed onto the rotatable rack.

In some embodiments, the ISM device comprises a CCD microscopic camera and a light source which are separated from the culture media in the bioreactor by the window.

Described herein, in some embodiments, is a bioreactor configured to culture cells. The bioreactor comprises a base and a lid. The base comprises two opposing curved or convoluted surfaces, two opposing flat surfaces, and a window disposed on one of the flat surfaces, the window having a higher degree of transparency compared to other portions of the base, wherein images or videos of cells are captured through the window by ISM device. The lid is attached or attachable to the base, the lid comprising a semipermeable membrane and a Luer connector that attaches to an external device.

In some embodiments, the external device comprises a stirrer or an impeller, and the bioreactor further comprises an edge computing processor (ECP) configured to control a rotational speed, or a duration of the stirrer based on a density or a morphology of the cells within the bioreactor.

In some embodiments, the external device comprises a liquid injection device, and the bioreactor further comprises an ECP configured to control an amount of culture medium to be injected into the base by the liquid injection device based on a density or a morphology of the cells within the bioreactor.

In some embodiments, the external device comprises a liquid injection device, and the bioreactor further comprises an ECP configured to control an amount of a buffer to be injected into the base by the liquid injection device based on a density or a morphology of the cells within the bioreactor, in order to regulate nutrients, pH, and other chemical variables of the culture medium within the bioreactor.

In some embodiments, the bioreactor further comprises a rack upon which the bioreactor is attached or embedded, and an ECP configured to control a parameter associated with a rotation, a vibration, a shaking, or a vortex of the rack based on a density or a morphology of the cells within the bioreactor.

These and other features of the bioreactors, apparatuses, systems, assemblies, methods, processors, and non-transitory computer readable media disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for purposes of illustration and description only and are not intended as a definition of the limits of the invention.

BRIEF DESCRIPTION OF THE DRAWINGS

Certain features of various embodiments of the present technology are set forth with particularity in the appended claims. A better understanding of the features and advantages of the technology will be obtained by reference to the following detailed description that sets forth illustrative embodiments, in which the principles of the invention are utilized, and the accompanying drawings of which:

DETAILED DESCRIPTION

Figure 1A:
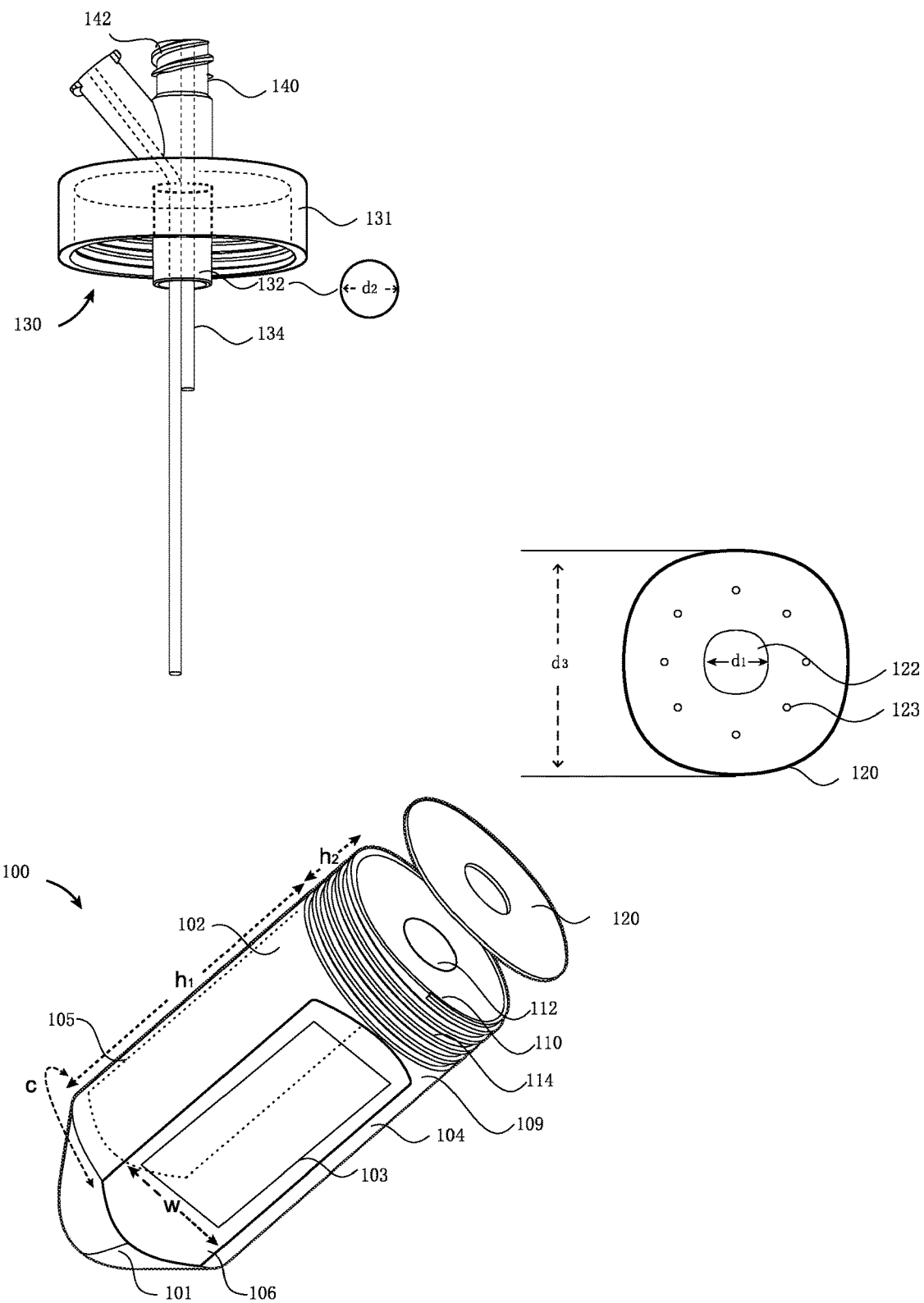
FIG. 1A illustrates an exemplary bioreactor that comprises curved surfaces opposing each other, in accordance with various embodiments.

Current batch or fed-batch bioreactors used to generate the expansion of cells include plates, flat-sided tissue culture flasks (e.g., T-flasks), Erlenmeyer flasks, spinner flasks, culture bags that are gas permeable and transparent, and hollow fibers. Some of the drawbacks of these current bioreactors may include limited versatility of adjusting culture conditions, insufficient online process monitoring and analytical compatibility, inability to facilitate different stages such as culturing and harvesting cells within a closed, sterile system, and noncompliance with Good Manufacturing Practices (GMP) standards. For example, critical process parameters and quality attributes of the cell expansion may need to be constantly monitored and responsively adjusted using process analytical technology (PAT) introduced by the FDA in their Guidance to the biotechnology, biopharma production, and the food industry in 2004. To implement PAT in conjunction with these current bioreactors, samples of cells may need to be withdrawn and analyzed outside of the bioreactors with an at-line or off-line analysis. As a result, not only might the density of the cells be reduced from having to remove samples of cells, but the growth of the cells may also be compromised by contamination to air and foreign matter such as viruses or bacteria. In addition, the constant exposure to the air may also render the growth conditions inconsistent over time. Because the growth of the cells includes many rounds of multiplication in order to obtain a feasible concentration or number of cells, a cumulative effect of having to open the plates may result in prolonged exposure to contaminants. More importantly, the at-line or off-line analysis cannot represent the real-time actual state of the bioreactor, which therefore causes imprecise understanding of the bioprocess variables. On-line analysis for real-time monitoring is therefore required. Additionally, these current bioreactors may be incompatible with all stages of cell culture and harvesting, such as centrifugation. In other words, these bioreactors may not be capable of being implemented within a centrifuge. This incompatibility necessitates a transfer to a separate bioreactor to perform different stages. The additional transfers may further compromise a sterility of the cell samples. In the foregoing, a novel bioreactor to address these limitations is described. This bioreactor will increase yield and proliferation rate by implementing PAT for on-line analysis of biological variables and responsive process control, while complying with GMP standards. Yield may be increased to $2*10^8$ cells to $10*10^8$ cells per bioreactor. In contrast, conventional yields may be less than $1*10^8$ cells per container. Such a bioreactor will further be compatible with most or all stages and functions of cell culture and harvesting, thus eliminating or minimizing a need to transfer cells to other bioreactors or instruments. The application of the bioreactor may be used in three most common cultivation modes in biomanufacturing which are batch, fed-batch, or perfusion.

In some embodiments, a bioreactor may include a container, receptacle, vessel, or repository, that is selectively permeable to air, such as oxygen, but impermeable to other foreign substances such as viruses or bacteria. A membrane attached or fastened to a lid of the bioreactor may selectively permit oxygen into while prohibiting viruses and bacteria from the bioreactor. The bioreactor may include two flat surfaces and two curved or convoluted surfaces, such as convex surfaces. At least one of the flat surfaces may include a microscopic window or an imaging window for ISM device. An ISM device may contact, or be in proximity to, the microscopic or imaging window in order to acquire an image or video of cells that are growing inside the bioreactor. Additionally, the two opposing curved or convoluted surfaces of the bioreactor would enable the bioreactor to maintain compatibility with other instruments such as a centrifuge. Thus, the cells may be centrifuged in a same bioreactor, thereby reducing a chance of contamination of the cells while promoting sterility. The bioreactor may have a conical or round bottom that forms a centrifuge head to maintain compatibility with a centrifuge. The bioreactor may also include a cap or a lid having a Luer interface, through which other devices such as a sensor probe, a stirrer, a liquid handling device such as a pipette or a pump-based media transfer, a cell retention device, a cell harvesting device, or a downstream bioreactor may be connected. The bioreactor may be connected, at its base, to a rack which may shake, vibrate, vortex, rotate, and/or translate the bioreactor to enhance growth productivity of the cells. These details will be elucidated in the foregoing FIGS.

Figure 1B:
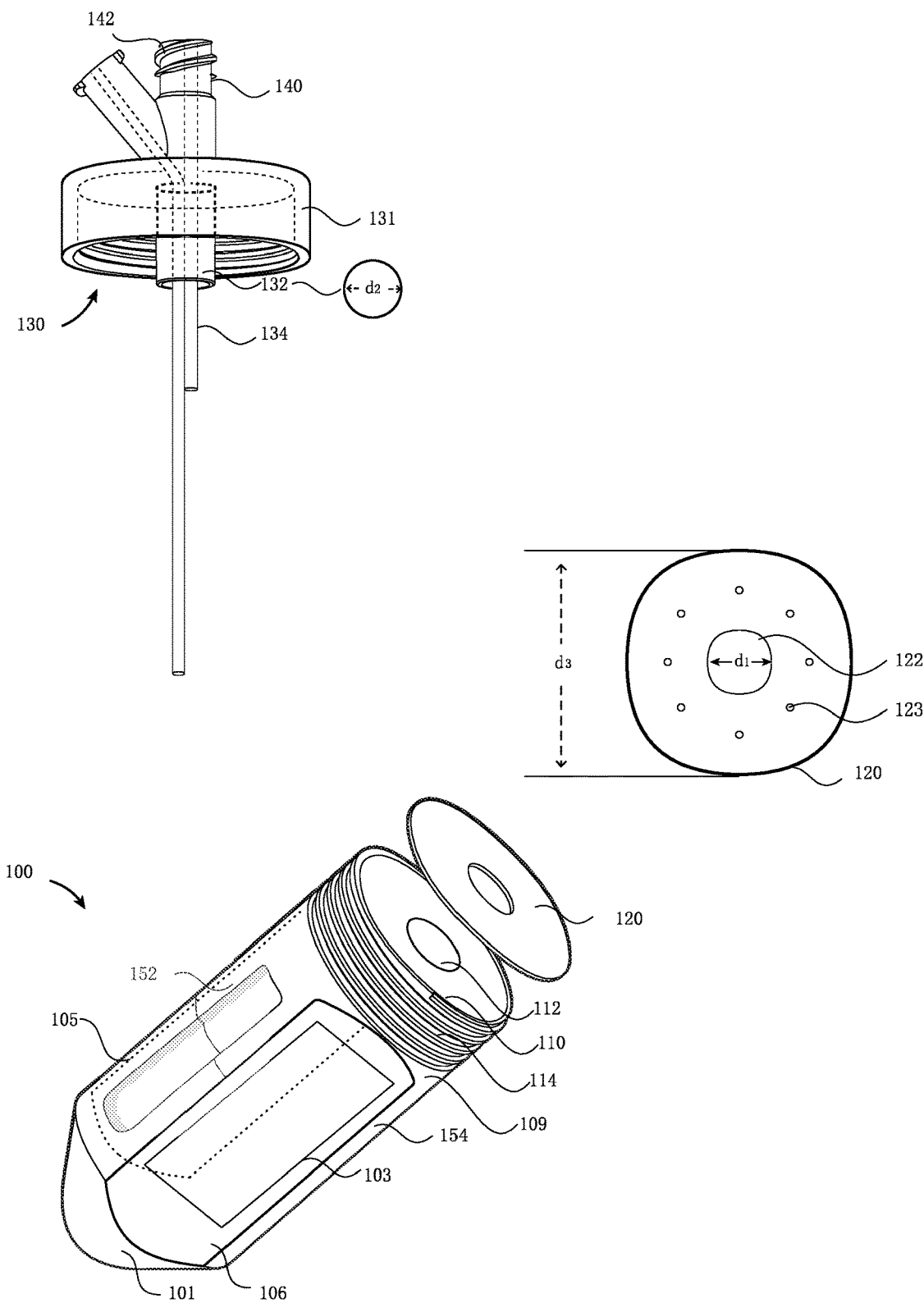
FIG. 1B illustrates an exemplary bioreactor that comprises convoluted surfaces opposing each other, in accordance with various embodiments.
Figure 1C:
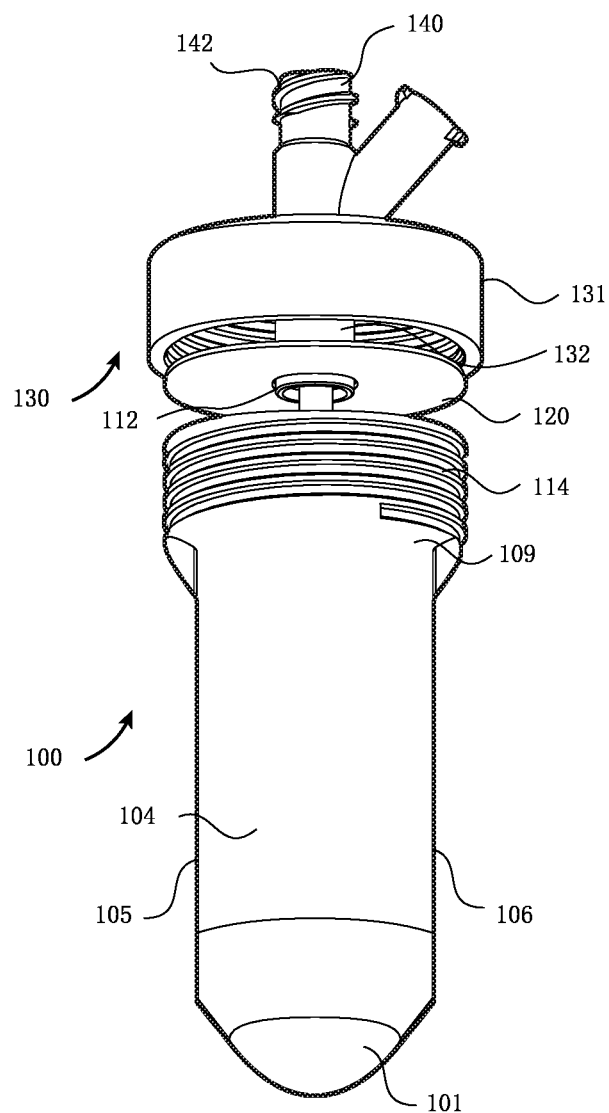
FIG. 1C illustrates a side view of the bioreactor as illustrated in FIG. 1A, to elucidate the rounded bottom of the bioreactor, in accordance with various embodiments.

FIG. 1A illustrates an exemplary bioreactor that includes a base 100 and a cap or lid 130 (hereinafter "lid"). The base 100 includes a bottom 101 that is conical or rounded in order to form a centrifuge head, as shown in FIG. 1C. The conical or rounded bottom may render the bioreactor compatible or conducive to a centrifuge, thereby further facilitating a closed system or operation, in which a range of operations such as centrifuging may be performed directly using the bioreactor without requiring a complex transfer from the bioreactor to a separate centrifuge tube. As illustrated in FIGS. 1A and 1B, the base 100 further includes surfaces 102, 104, 105, and 106 along a periphery of the base 100. The surfaces 105 and 106 may be flat surfaces opposing each other while the surfaces 102 and 104 may be curved surfaces opposing each other. The opposing curved surfaces 102 and 104 may enable the bioreactor to be compatible with other instruments, such as a centrifuge and a holding rack, and increase the viable culture space in which cells may grow. In some embodiments, each of the curved surfaces 102 and 104 may comprise, or consist of, a portion or a segment of a cylinder body, such as, between 5% and 50% of an entire cylinder body. For example, each of the curved surfaces 102 and 104 may comprise, or consist of, between 10% and 40% of an entire cylinder body, between 20% and 30% of an entire cylinder body, or around 25% of an entire cylinder body. In some embodiments, an arc length, denoted as c in FIG. 1A, of each of the curved surfaces 102 and 104 is between 0.5 and 2 times a width, denoted as w, of each of the flat surfaces 105 and 106. These aforementioned relationships between the arc length and the width of the flat surfaces, together with $h_1$, may be adjusted according to desired or target cell proliferation rate and yield by affecting cell-specific perfusion rate (CSPR). A lower CSPR indicates that more cells can be sustained with a certain amount of medium. As a particular example, a different cell proliferation rate and yield may be desired depending on a type of cell and/or a growth mechanism of that type of cell. In particular, T-cells may grow within the medium, while adherent cells may grow along walls. In some embodiments, the arc lengths of each of the curved surfaces 102 and 104 are approximately equal to each other, and approximately constant throughout a height $h_1$ of the curved surfaces 102 and 104. In some embodiments, as shown in FIG. 1B, convoluted surfaces 152 and 154 may oppose each other instead of the curved surfaces 102 and 104.

In some embodiments, the widths of the flat surfaces 105 and 106 are approximately equal to each other, and approximately constant throughout the height $h_1$ (e.g., at any height $h_1$) of the flat surfaces 105 and 106. Disposed on either or both of the flat surfaces 105 and 106 may be a window 103, a transparent rectangular region through which an image of an interior of the base 100 may be captured by an ISM device. The window 103 may take up the entire flat surface 106 or nearly the entire flat surface 106, while excluding boundaries or margins of the flat surface 106, such as 2 mm boundaries along one or more dimensions. The window 103 may have a higher transparency and a thinner thickness compared to other portions (e.g., boundaries) of the flat surfaces 105 and 106, and the base 100. The window with thinner thickness is beneficial to shorten the working distance of ISM device from the microscopic lens to the cells so as to focus most cells inside the view. Further details of the window 103 will be described in FIGS. 4A and 4B. For example, a high-resolution image or continuous frames of cells within the interior of the base 100 may be captured through the window 103.

The base 100 may, in some embodiments, optionally further include a plate or separator (hereinafter "plate") 110 that includes a hole or perforation (hereinafter "hole") 112. The plate 110 may partition the base 100 into two segments or portions, a lower portion that includes the flat surfaces 105 and 106 and the curved surfaces 102 and 104 (or convoluted surfaces 152 and 154), and an upper portion that includes a periphery 114. The plate 110 contacts the top portions of each of the curved surfaces 102 and 104, and the flat surfaces 105 and 106. Meanwhile, fluids or other substances may be introduced into, and/or extracted or removed from, the base 100 through the hole 112. The plate 110 may include two curved edges that match a curvature of and contact the curved surfaces 102 and 104, and two flat edges that are aligned with and contact the flat surfaces 105 and 106. Additionally, an upper portion of the base 100 may include the periphery 114, as alluded to. The periphery 114 may be cylindrical and may form a cylindrical shell. A diameter of the periphery 114 may be constant throughout a height $h_2$ of the periphery 114. The diameter of the periphery 114 may be approximately equal to, or slightly less than, a diameter of the curved surfaces 102 and 104. For example, the diameter of the periphery may be between 0.5 and 1.5 times the diameter of the curved surfaces 102 and 104. In some embodiments, the diameter of the periphery 114 may exceed a distance, for example, a shortest distance, between the flat surfaces 105 and 106. For example, the diameter of the periphery may be between 1 and 5 times of the shortest distance between the flat surfaces 105 and 106. In some embodiments, a transition or overhang 109 (hereinafter "overhang") may be disposed at a junction between the periphery 114 and the curved surface 104. A same or corresponding overhang may also be disposed at a junction between the periphery 114 and the curved surface 102 (not shown for simplicity).

A lid 130 may be fastened, fitted, or secured (hereinafter "secured") over the periphery 114 of the base 100. In FIG. 1A, the lid 130 is shown separated and disassociated the base 100, while in FIG. 1C, the lid 130 is shown secured to the base 100. In some embodiments, the lid may be sealed to the base 100 upon attachment using, for example, a sealing member such as an O-ring. In some embodiments, the lid 130 may include an outer shell 131 (hereinafter "shell"). An inner surface of the shell 131 may fit over an exterior of the periphery 114 to couple the base 100 to the lid 130. In some embodiments, the lid 130 may include a shaft or column 132 (hereinafter "shaft") extending circumferentially outward from a center of the lid 130. The shaft 132 may extend into the hole 112 of the base 100. The shaft 132 may include a channel or an open space 134 (hereinafter "channel") located around, or alternatively, offset from, a center of the shaft 132. Through the channel 134, a rod, connector, or extension (hereinafter "rod") that connects to an external device such as a liquid handling device (e.g., pipette) or a mixer may pass through. The device may perform operations on the fluid within the base 100 when the lid 130 is secured onto the base 100. In other embodiments, no rod that connects to an external device may be inserted through the channel 134, but rather, a stream of liquid, such as a culture medium, may be injected through the channel 134.

In some embodiments, a polymer membrane made of PTFE 120 (hereinafter "membrane"), which may include a ring, may be attached snugly or secured around the shaft 132. The membrane 120 may include a polymer ring and optionally, a gap 122. The gap 122 may have a diameter $d_1$. The gap 122 may result in reducing a surface area or size of the membrane 120, which may reduce a ratio of a size of the membrane 120 to a height of cell culture medium, thereby facilitating an increase of cell density, proliferation rate, and/or yield of cells. The membrane 120 may include perforations 123 (hereinafter "perforations") as an ultrafiltration tool which render the membrane 120 selectively permeable to oxygen but impermeable to other biological substances such as viruses and bacteria. The selective permeability of the membrane 120 to oxygen permits a culture or growth medium within the base 100 to be sufficiently oxygenated, which eliminates the integration of a gas pipe offering gas flow. Given that a diameter of the shaft 132 is $d_2$, the membrane 120 may be secured around an exterior of the shaft 132 at a position where $d_1$ equals $d_2$ as shown in FIG. 1C. In some embodiments, a position of the membrane 120 relative to a bottom of the base 100, at the rounded bottom, 101, is more than halfway of a distance from the rounded bottom 101 to a top of the connector 140. In other words, the membrane 120 may be disposed closer to the top of the connector 140 than to the rounded bottom 101. In some embodiments, a position of the membrane 120 relative to a bottom of the base 100, at the rounded bottom, 101, is more than three-quarters of the distance from the rounded bottom 101 to the top of the connector 140. Due to the membrane 120 being positioned nearer the top of the connector 140, a height of a cell or growth medium within the bioreactor may be increased. If the membrane 120 were positioned nearer the rounded bottom 101, then a height of a cell or growth medium would be lower so as to avoid traversing the membrane 120. An increased height of the cell medium is conductive to a higher cell density and yield.

In some embodiments, the diameter $d_2$ of the shaft 132 may be constant throughout a length of the shaft 132. In other embodiments, the diameter $d_2$ of the shaft 132 may be varying throughout the length of the shaft 132. For example, the diameter $d_2$ of the shaft 132 may be increasing towards the connector 140 (e.g., a distal end) and decreasing away from the connector 140 (e.g., a proximal end). A rate of increase of the diameter $d_2$ of the shaft 132 may be constant or linear. In some embodiments, the rate of increase of the diameter $d_2$ of the shaft 132 may be increasing according to a step function. In some embodiments, rather than being secured around the exterior of the shaft 132, the membrane 120 may be secured within an inner surface of the channel 134, at a position where an outer diameter $d_3$ of the membrane 120 equals a diameter of the channel 134.

Disposed at the distal end of the lid 130 may be the connector 140. The connector 140 may be a male connector and include a Luer interface having metric threads 142, and/or some other mechanism such as a tapered outer surface by which an external device may be secured onto the connector 140. Thus, an external device may perform operations on the bioreactor simply by seamlessly interfacing with the connector 140, thus avoiding potential contaminations while ensuring a closed system or operation. On the other hand, if the external device requires a separate transfer to another container to conduct off-line manipulations or analysis, such a scenario would deviate from a closed system or operation and further introduce a potential of contamination, and/or compromise a growth, yield, or proliferation of cells.

Such an external device may include a mixer, a stirrer, or a liquid handling or liquid transfer device used in culture or growth medium exchange or harvesting. For example, in FIG. 2, a customized pipette or syringe 200 may be secured onto the connector 140. In some embodiments, the lid 130 may include multiple Luer interfaces, each of which may connect to a different external device. For example, one Luer interface may be connected to a mixer, a second Luer interface may be connected to a liquid handling device such as a pipette or syringe, and a third Luer interface may be connected to a cell harvest device.

Figure 3A:
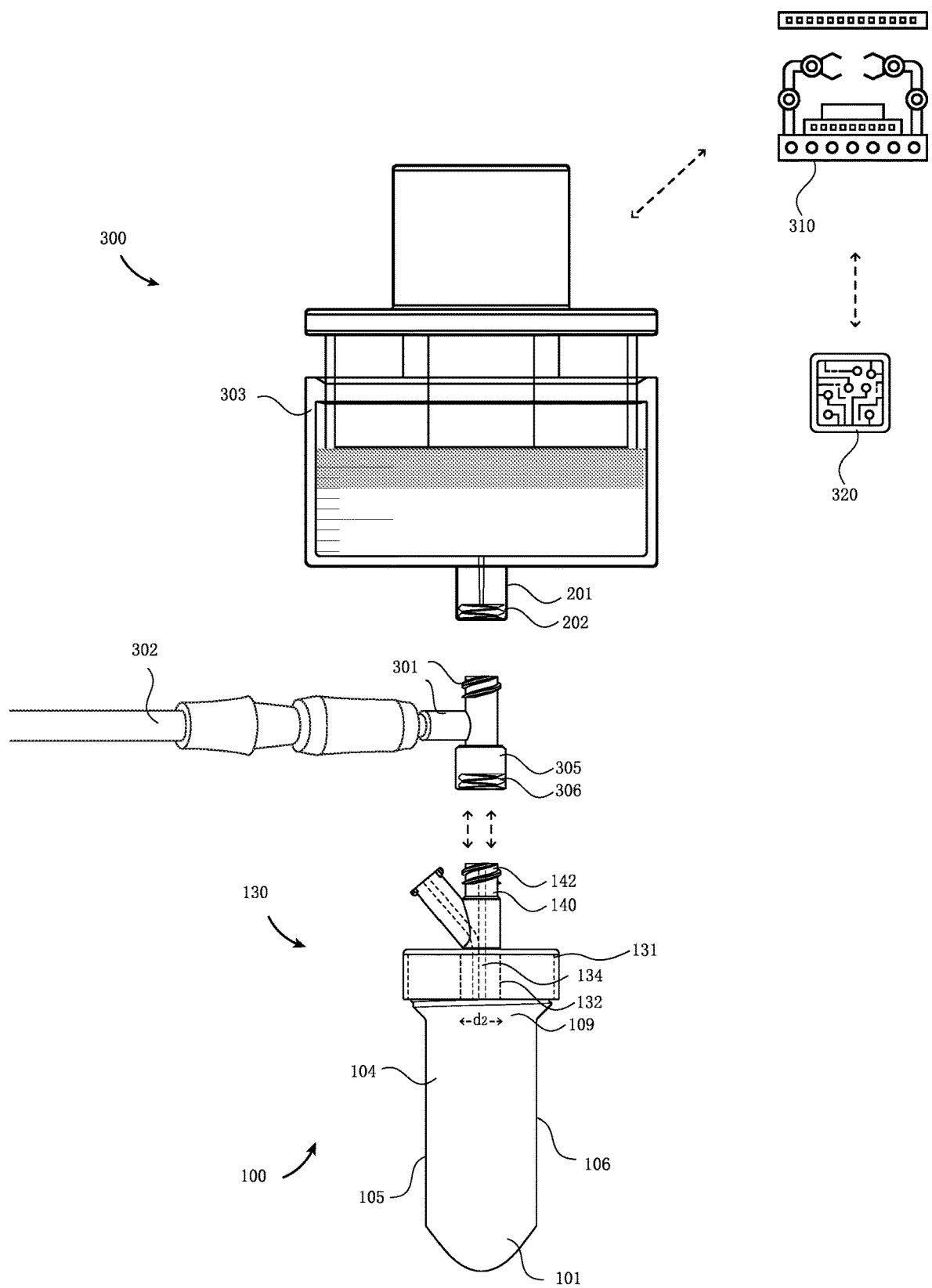
FIG. 3A illustrates an external device, here, a liquid exchange device being secured onto a connector of the bioreactor as illustrated in FIGS. 1A and 1C, in accordance with various embodiments.

The pipette or syringe 200 may include a female connector 201 that includes compatible threads 202 and/or a tapered inner surface. The female connector 201 may complement and be secured onto the connector 140 via the threads 202 in order to seamlessly inject fluid into the base 100 or extract fluid from the base 100 for liquid transfer in a way of closed manipulation. Another example of an external device is shown in FIG. 3A, in which a liquid transfer device 300 may transfer a portion or all of the liquid from the base 100, through the lid 130, into a target container or bioreactor with a larger volume compared to the bioreactor. A female connector 305 of the liquid exchange device 300 may be directly attached, fastened, or secured onto the connector 140 using threads 306 or other fastening or securing mechanisms that complement the threads 142 or other fastening or securing mechanisms on the connector 140.

The liquid from the base 100 may be transferred into the target container or bioreactor via an Luer lock interface 301 and a connector 302. In some embodiments, the interface 301 may include a T-connector, and may be hermetically sealed using a sealing member. In some embodiments, the interface 301 may include one or more check valves to permit fluid to flow from the base 100 to the syringe 303, from the base 100 through the connector 302, and/or from the syringe 303 to the connector 302 but prohibit fluid from flowing in directions from the syringe 303 to the base 100, or from the connector 302 to the base 100. Additionally, fluid may flow from the base 100 through the interface 301 to the syringe 303, where the fluid may be measured before being transported through the interface 301. The flow or transport of the fluid from the base 100 may be controlled by an automated system or a robotic system 310, which may conduct adaptive interactions with the syringe 303 based on the automated protocol of extracting fluid from the base 100 and releasing the fluid to the connector 302. The automated system may include a mobile slideway, a mechanical arm, and a connected actuator. The robotic system 310 may include a robotic arm with multiple degrees of freedom, and a gripper. The automated or robotic system may automatically communicate with a decision-making processor 320 (hereinafter "ECP") via the network protocol to propose requests and receive responses. The ECP 320 may include any one or combination of hardware, firmware, or software, and may be implemented as any one or combination of a central processing unit (CPU), graphics processing unit (GPU), field-programmable gate array (FPGA), or application-specific integrated circuit (ASIC). As will be described further in reference to FIGS. 4A, 4B, and 5, the processor 320 may control the automated system or robotic system to perform precise operations of extracting fluid from and/or transmitting fluid to the connector 302 based on PAT analyses beyond captured cell images. For example, the processor 320 may proactively determine subsequent actions of the timing, contacting duration, speed, accelerated velocity, and rotations, etc. in the process of liquid handling based on an analysis of density and/or morphology of currently growing cells within the base 100.

Figure 2:
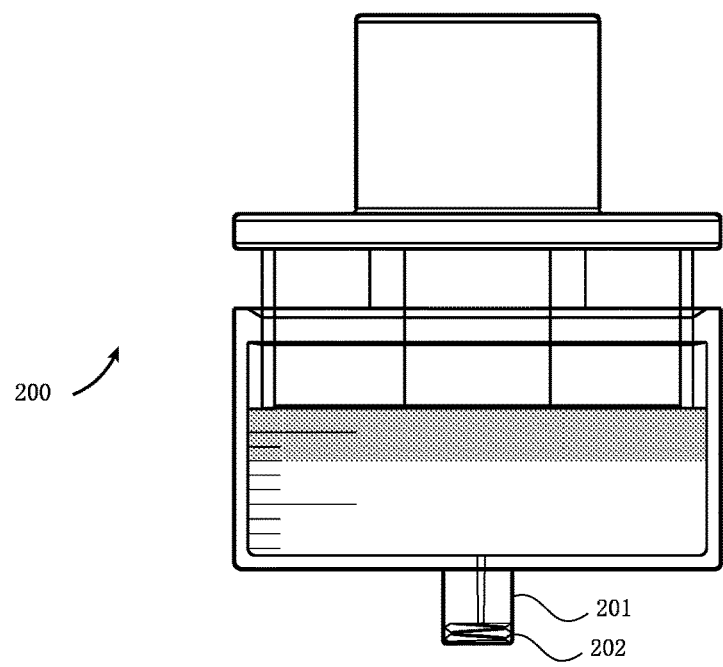
FIG. 2 illustrates an external device, here, a pipette or a syringe being secured onto a connector of the bioreactor as illustrated in FIGS. 1A and 1C, in accordance with various embodiments.
Figure 2:
Figure 2:
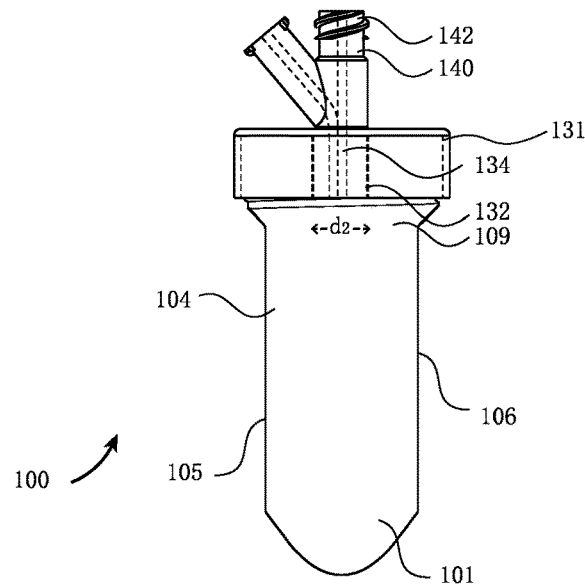
Figure 3B:
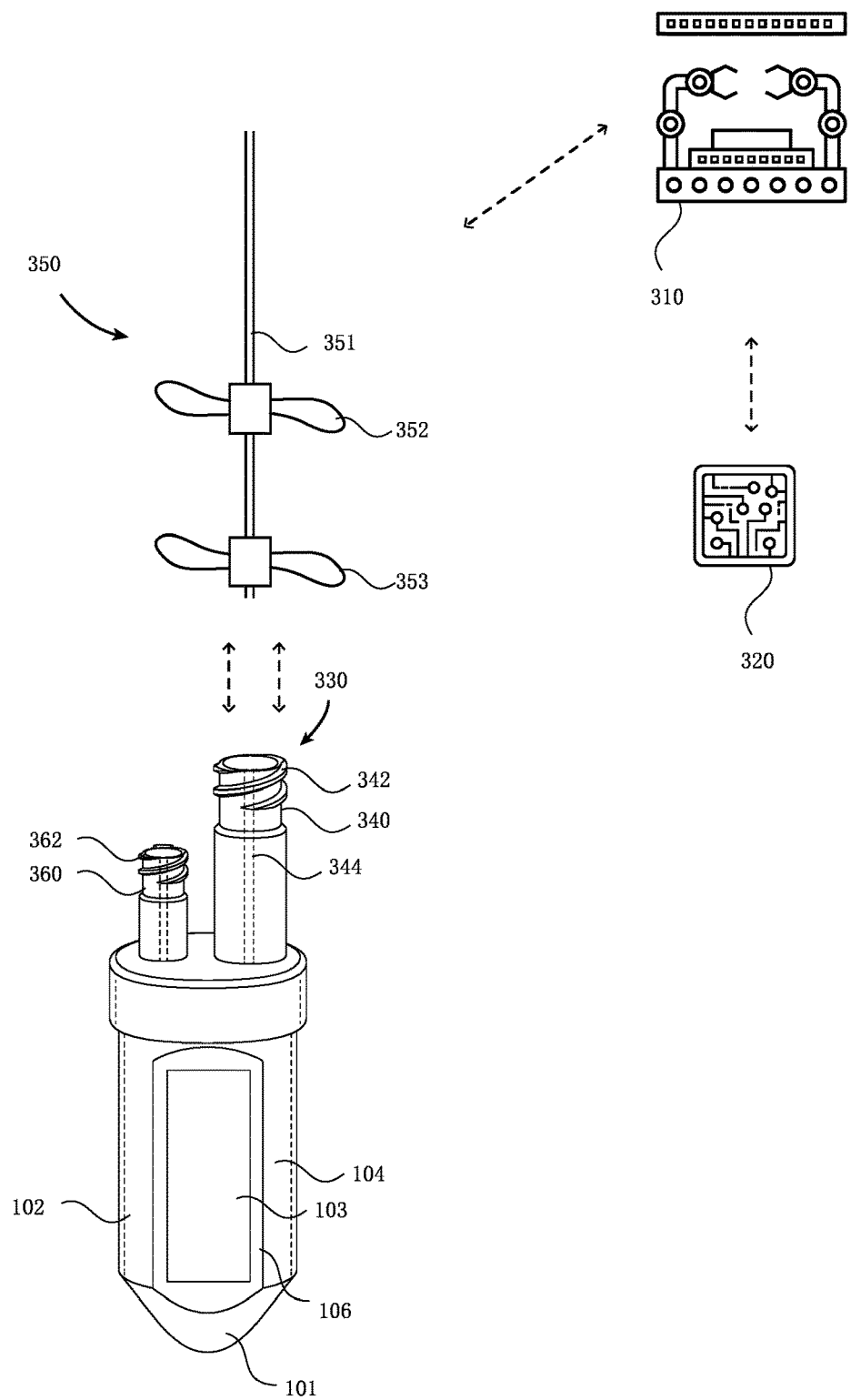
FIG. 3B illustrates an external device, here, a stirrer or mixer being secured onto a connector of the bioreactor as illustrated in FIGS. 1A and 1C, in accordance with various embodiments.
Figure 4A:
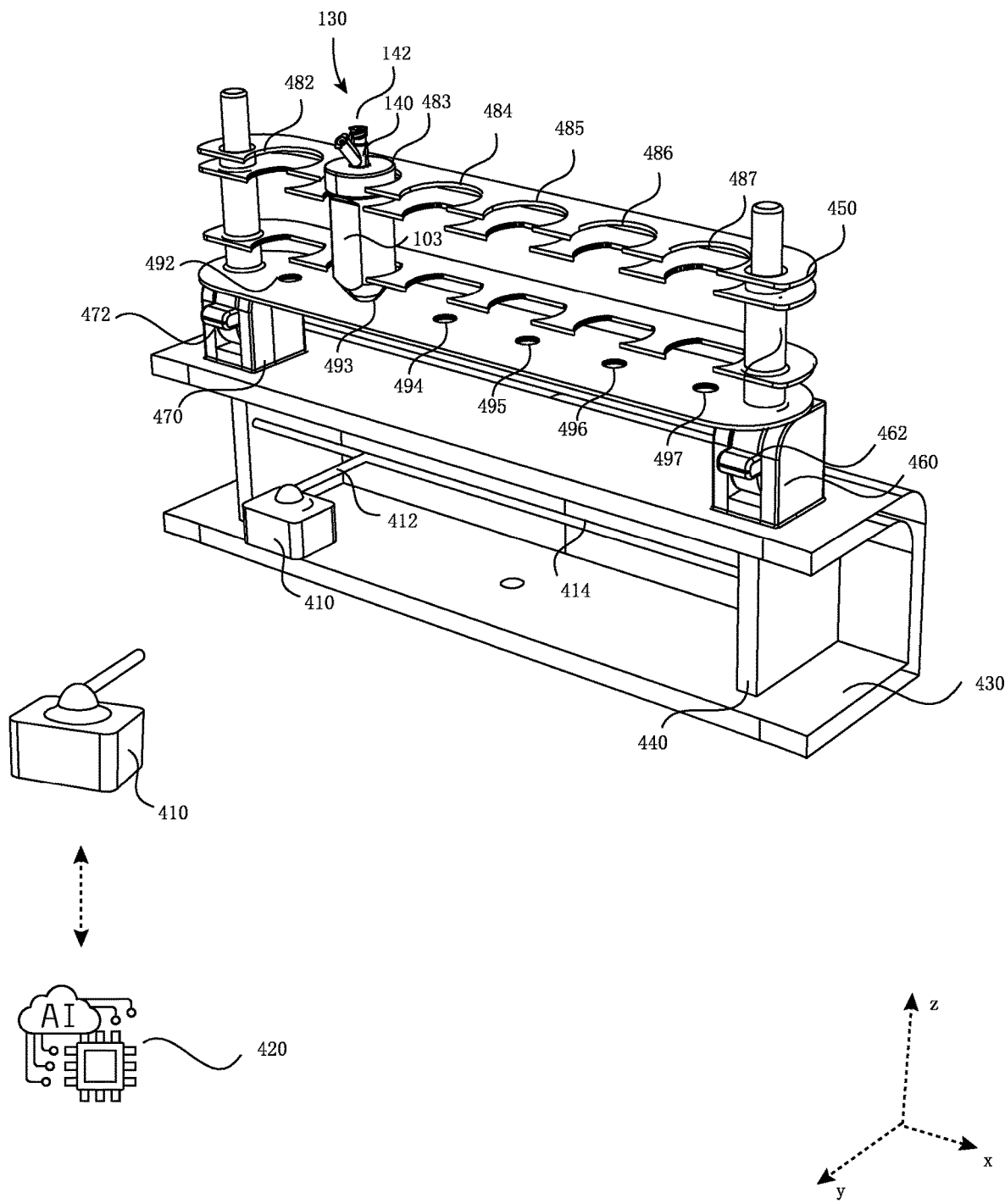
FIG. 4A illustrates an accompanying rack upon which the bioreactor is fixed in an upright position or orientation, in accordance with various embodiments.
Figure 4B:
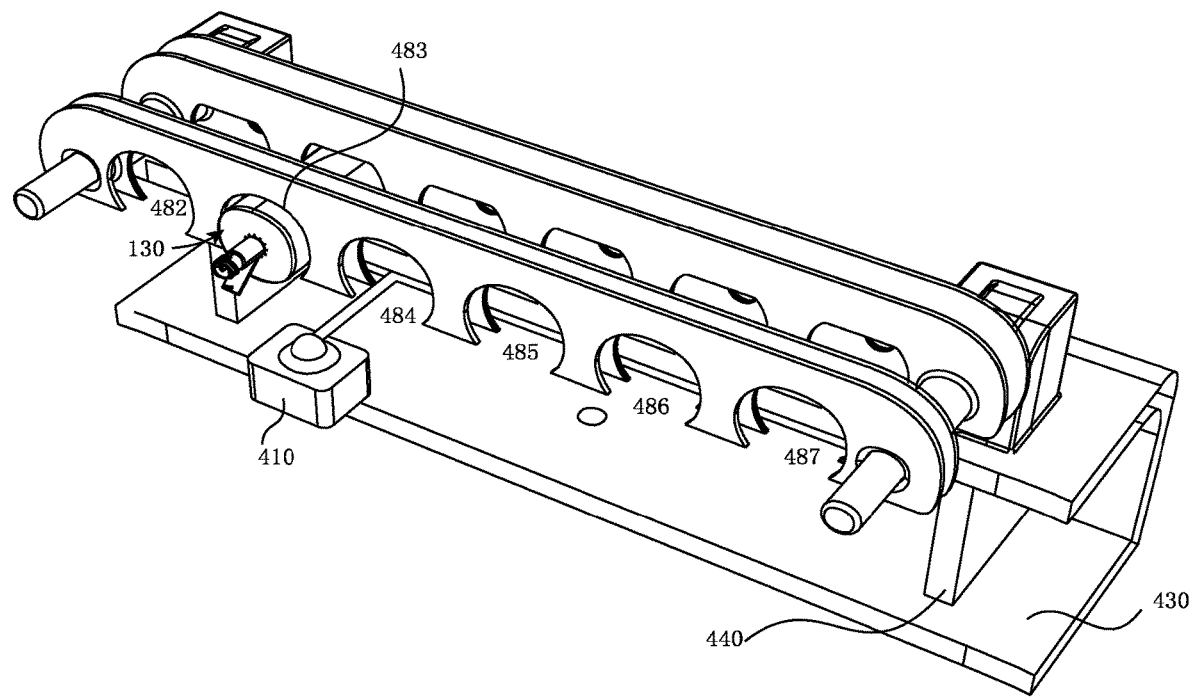
FIG. 4B illustrates an accompanying rack upon which the bioreactor is fixed in a horizontal position or orientation, rotated 90 degrees clockwise from that shown in FIG. 4A, in accordance with various embodiments.

Yet another example of an external device 350, as shown in FIG. 3B, may be one or more stirrers, impellers or mixers 352 and 353 attached over a rod 351. The rod 351 may be securely positioned and/or fixed onto a connector 340 (e.g., a larger Luer connector) of a lid 330, or other fastening or securing mechanisms. Thus, the stirrers or mixers 352 or 353 may be integrated with the lid 330 via a separate, larger Luer connector (e.g., the Luer connector 340) compared to the Luer connector 140. Alternatively, the stirrers or mixers 352 may be pre-installed within the bioreactor 100 and adapted to integrate the connector 340. Threads 342 of the Luer connector 340 and a channel 344 may be optional. Additionally, the lid 330 may include a Luer connector 360 having threads 362, which may be implemented in a similar or same manner as the connector 140 having the threads 142. Operations of the mixers 352 and 353, such as a rotational speed and/or durations or cycles of rotation, may be controlled by the automated or robotic system 310, which may in turn be under control of the processor 320. In some embodiments, the stirrers or mixers 352 and 353 may be already positioned on the rod 351. The insertion or positioning of the stirrers or mixers 352 or 353 may be controlled by the automated or robotic system 310. Therefore, as shown in the examples of FIGS. 2, 3A, and 3B, the connector 140 may be adapted or configured to seamlessly fit and connect a variety of different devices to perform fluid exchange, extraction, or other treatment of the fluid within the base 100 without having to open the lid 130. FIGS. 4A-4B illustrates an exemplary embodiment in which the bioreactor, which includes the base 100 and the lid 130, may be positioned onto a rotatable rack 450 (hereinafter "rack"). The embodiment illustrated in FIGS. 4A-4B may be implemented in conjunction with any of the embodiments illustrated in FIGS. 1A and 1C, FIG. 1B, FIG. 2, FIG. 3A, or FIG. 3B. In particular, the bioreactor may be fitted within holes 483 (not shown clearly, obscured by the bioreactor) and the 493. The rack 450 may further include the upper layer of holes (482, 484, 495, 486, 487) and lower layer of holes (492, 494, 495, 496, 497). The upper layer holes cultivate the framework of the base 100 to circumscribe the bioreactor for a stable placement. The lower layer holes are in form of a circle fitting the size of a cross-section of rounded or conical bottom 101. A pair of upper hole and lower hole render the stability of the bioreactor to facilitate the automated or robotic manipulations. Different bioreactors may be fitted or placed onto each of the aforementioned pairs of holes. The rack 450 may be secured onto a supporting base or platform 430. A mechanical rocking module including a supportive structure 470 and a rotating motor component 472, and a second rocking system including a supportive structure 460 and a rotating motor component 462, may be attached between the rack 450 and the platform 430 and used to control a translation, rotation, and/or alignment of the rack 450 with respect to the platform 430. A translation and/or rotation of the rack 450 may be used to adjust an orientation and/or position of the bioreactor to capture cell images within the base 100. In particular, FIG. 4A illustrates that the rack 450 is in an upright position. Meanwhile, in FIG. 4B, the rack 450 has been rotated 90 degrees clockwise. In some embodiments, the rack 450 may be rotated by up to 90 degrees clockwise or counterclockwise with respect to the platform 430 from the upright orientation as shown in FIG. 4A. Rotating the rack by 90 degrees clockwise may facilitate imaging of cells within the bioreactor through the window 103. In some examples, an ISM device 410, which may include a microscope, may be positioned directly below the window 103 and acquire images or videos of cells through the window 103. In other embodiments, the ISM device 410 may be positioned directly above the window 103. The ISM device 410 may be secured and attached to a sliding rail 414 via a rod 412. The rod 412 may further be rotatable about an x-axis and/or a y-axis, extensible along a z-axis, and/or translatable along the x-axis. Movement or rotation of the rod 412 may be controlled, for example, by a processor 420 such as an ECP. The processor 420 may include any one or combination of hardware, firmware, or software, and may be implemented as any one or combination of a central processing unit (CPU), graphics processing unit (GPU), field-programmable gate array (FPGA), or application-specific integrated circuit (ASIC). The control of the rod 412 may be based on analyses of images or videos taken by the ISM device 410. For example, if images or videos of the bioreactor fail to focus on a large number of cells or satisfy a given threshold resolution, the rod may be moderately translated, rotated, and/or moved at the scale of millimeter-level movement to obtain an image or video from a different perspective and working distance. In conjunction, the rack 450 may also be rotated so that the ISM device 410 may capture another perspective of the image or video. If additional bioreactors are positioned within the holes 482 and 492, holes 484 and 494, holes 485 and 495, holes 486 and 496, and holes 487 and 497, the ISM device 410 may successively capture images or videos of each of the bioreactors and be translated along the x-axis to capture images or videos of subsequent bioreactors. Therefore, images or videos of cells within the window 103 may be acquired or captured and analyzed without extracting a sample from the bioreactor, which further facilitates a closed system or operation while reducing a risk of contamination. The real-time captured images representing the biomass variables of different bioreactors on the rack 450 ensure the online analysis of the biological characteristics, which increases the efficiency of PAT-aided cell culture process. Consequently, perspectives or other parameters used to acquire the images or videos may be iteratively adjusted or recaptured based on the online PAT analysis.

The rail 414 may include an indentation or cavity into a surface of an island 440 of the platform 430. The island 440 may include an open or empty gap or space in a center of the platform 430. The island may be rectangular in shape. Although not shown for simplicity, each of the four surfaces of the island 440 may include a rail similar or same to the rail 414, along which the ISM device 410 may move.

Therefore, the ISM device 410 may capture images or videos of cells within the bioreactor, without even extracting a liquid sample from the bioreactor. Such a streamlined image capture and analysis mechanism may further ensure compliance with GMP standards while reducing a possibility of contamination. Additionally, following PAT-based analysis of the captured videos or images, the imaging settings may be further adjusted via a rotation of the rack 450 and/or an adjustment of a position and/or angle of the imaging device 410. Moreover, following PAT-based analysis of the captured videos or images, the growth conditions of cells within the bioreactor may be proactively perceived and adaptively configured or manipulated by adding or reducing an amount of a culture or growth medium, or performing mechanical perturbations such as shaking, vibrating, vertexing, or rotating the bioreactor.

Figure 5:
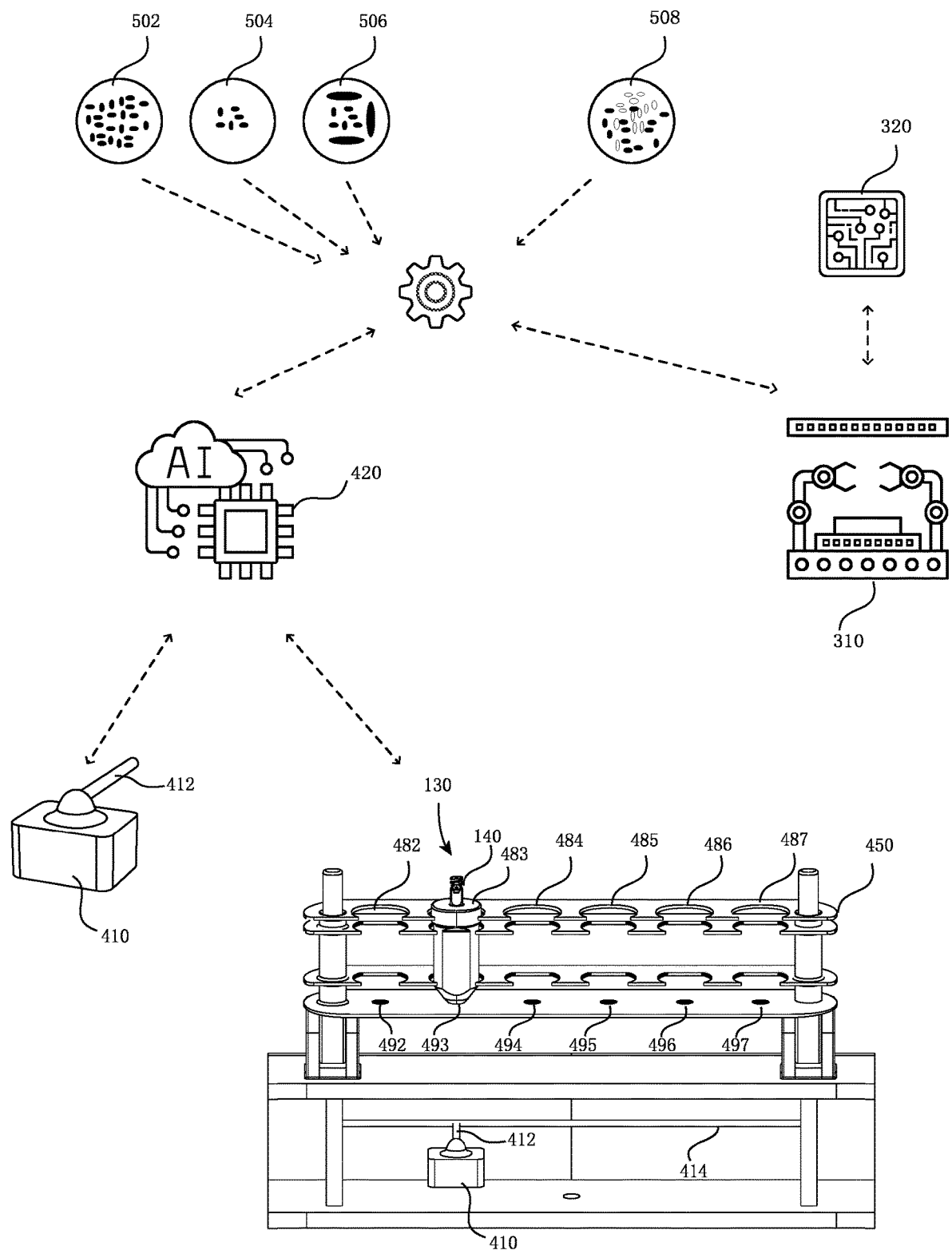
FIG. 5 illustrates an exemplary process flow diagram illustrating how analysis of images or videos of cells within the bioreactor is used to adjust a setting or parameter of an external device connected to the bioreactor of FIGS. 1A and 1C, a rotation, vibration, shaking, vortex, translation, or other setting of an accompanying rack upon which the bioreactor is fixed as shown in FIGS. 4A and 4C, and/or a setting of an imaging device.

FIG. 5 illustrates a systematic process by which ISM imaging settings within the bioreactor, and/or growth conditions within the bioreactor, may be seamlessly adjusted without having to open the lid 130 and/or extract a sample. In particular, images or videos 502, 504, 506, and/or 508 may be acquired through the window 103 using the ISM device 410. The images or videos 502, 504, 506, and/or 508 may be analyzed, for example, using a processor 510. The edge computing processor 510 deployed at the local working station may include a machine learning or deep learning model that further includes neural networks, such as a convolutional neural network (CNN) for image-based prediction tasks like cell recognition, detection, segmentation, and tracking. Results from the machine learning-based predictive models may be fed to the processors 320 and/or 420. The analysis may include determining a resolution of the images or videos 502, 504, 506, and/or 508, detecting biomass variables which are mainly cell density and morphology, and whether the cells are properly expressing a target protein, which may be based on a level of fluorescence. The analysis may, additionally or alternatively, include determining a rate of bioactivity change overtime, from different image and/or video frames, of the cell density and/or parameters associated with the morphology, such as cell width, and/or a rate of change over time of the expression of the target protein.

In some embodiments, the processor 320 may control the automated or robotic system 310 based on the analysis. In some examples, the control of the automated or robotic system 310 may be used to adjust rotation speed or rotation cycles or settings of the mixers or stirrers 352 and 353 connected to the automated or robotic system 310, as shown in FIG. 3B. In particular, if the analysis reveals, suggests, or indicates nonuniform growth conditions, the mixers or stirrers 352 and 353 may be caused, by the processor 320, to operate at higher rotational velocity and/or frequency. In some examples, the control of the automated or robotic system 310 may entail controlling a rate at which a culture or growth medium is injected into or extracted from the base 100, for example, using the pipette or syringe 200 as shown in FIG. 2. In particular, if the analysis reveals, suggests, or indicates that a cell density is below a threshold, and/or that cell morphology is abnormal (e.g., a deviation in a parameter, and/or a parameter of the cells, such as width, is outside of a threshold), then more culture or growth medium may be injected into the base 100. In addition, the automated or robotic system 310 may further increase an amount of oxygen flowing into the base 100. If, on the other hand, the analysis reveals, suggests, or indicates that the cell density is above a threshold, then the automated or robotic system 310 may cause a culture or growth medium to be extracted from the base 100. In some examples, if a cell density has reached a threshold, the arm 310 automated or robotic system cause cells and/or a culture or growth medium within the base 100 to be transferred to a larger container or bioreactor via the liquid exchange device 300.

In some embodiments, the processor 320 may control one or more automated or robotic systems or other mechanisms to regulate other parameters such as physiochemical parameters including temperature, pH, dissolved oxygen concentration, and osmolarity of the culture or growth medium. For example, an automated or robotic system may regulate an injection of buffers such as NaOH (sodium hydroxide) or HCl (hydrochloric acid) in order to regulate a pH of the culture or growth medium. In some examples, relative concentrations and/or absolute amounts of sodium bicarbonate ($NaHCO_3$), HEPES (4-(2-hydroxyethyl)-1-piperzaine ethanesulfonic acid), phenol red, protein, amino acids, carbohydrates, lipids, inorganic salts, vitamins, B-mercaptoethanol, or growth factors such as interleukin-2 (IL-2), may be adjusted within the culture or growth medium.

In some embodiments, the processor 420 may control an operation of the rod 412 and/or of the motors comprised of 470 and 472, and 460 and 462, based on the analysis of the images or videos 502, 504, 506, and/or 508. In some examples, the processor 420 may, upon determining that the images or videos 502, 504, 506, and/or 508 satisfy a threshold resolution, in which a density and/or morphology of cells is reliably detectable, the processor 420 may cause the rod 412 to be translated along the rail 414, as illustrated in FIGS. 4A and 4B, so that the ISM device 410 can capture images or videos of a subsequent bioreactor (such as, a bioreactor placed into the holes 484 and 494). In some examples, the processor 420 may, upon determining that the images or videos 502, 504, 506, and/or 508 fail to satisfy a threshold resolution, rotate the arm 412 about an x-axis and/or y-axis, or extend or contract the arm 412, to obtain different perspectives through the window 103, as alluded to with respect to FIGS. 4A and 4B. In some examples, the processor 420 may, right before images or videos are to be captured through the window 103, rotate the rack 450 by 90 degrees clockwise with respect to its upright position via two rocking modules comprised of 470 and 472, and 460 and 462. In some examples, the processor 420 may, upon determining that the images or videos 502, 504, 506, and/or 508 fail to satisfy a threshold resolution, cause a rotation and/or translation of the rack 450 via the rocking modules comprised of 470 and 472, and 460 and 462. In some examples, the processor 420 may, upon determining that the images or videos 502, 504, 506, and/or 508 fail to satisfy a threshold resolution, cause a rotation and/or translation of the rack 450 via the rocking modules comprised of 470 and 472, and 460 and 462. In some examples, if the analysis of the images or videos 502, 504, 506, and/or 508 reveals, suggests, or indicates that the cell density is below a threshold and/or that the cells have an abnormal morphology, the processor 420 may cause the bioreactor to shake, vibrate, vortex, rotate, and/or translate, via the motors comprised of 470 and 472, and 460 and 462 in order to adjust growth conditions of the cells. For example, the processor 420 may control a speed, frequency, and/or duration of shaking, vibration, or vortex. In particular, the processor 420 may adjust a rocking cycle of the rack 450 in an attempt to increase efficiency of gas transfer, control an amount or rate of gas exchange between a surface of the culture or growth medium and a pericellular level, or change shear conditions depending on a cell type. For example, sensitive cell types may need to grow under low shear conditions. As a result of the foregoing, imaging conditions or settings, and growth conditions of the cells, may be seamlessly and automatically adjusted as a result of an analysis of cell images or videos within the bioreactor to improve proliferation rate.

In some embodiments, the machine learning component 510 may be trained to infer the cell presence and cell density of images or videos 502, 504, 506, and/or 508, and/or morphology of cells within the images or videos 502, 504, 506, and/or 508, and/or bioactivity over time of cells within the images or videos 502, 504, 506, and/or 508. The training process may entail multiple sets of training data captured from local working station to serve different predictive tasks. A first predictive task trained with cell images having labeled alive single cells may be detecting cell presence from captured images or videos utilized the trained machine leaning component 510. Alive single cells are detected and circumscribed from an image or video frame. Visualizing the highlighted bounding boxes of detected alive single cells may provide a global composition or distribution of cultivated cells. Summing up all detected single cells from an image can calculate the cell amount and averaging the cell number of images captured from distributed perspectives on window 103 can figure out the synthesized cell number. Using a specific formula can further calculate cell density. The real-time calculated cell density may be used to determine whether the online analysis of cell density satisfying an acceptable threshold or not. A second predictive task trained with cell images having labeled morphology types may be recognizing the type of cell morphology such as normal, abnormal, or other defined morphological categories. Thus, the machine learning component 510 may be trained to recognize information on cell morphology of images or videos 502, 504, 506, and/or 508 to reflect the real-time biological conditions within different bioreactors. Cell morphology may be determined to be normal further on the basis that respective deviations of the parameters of the cells are within acceptable ranges. Meanwhile, a third predictive task may be determining the bioactivity over time in the bioprocess. Based on the previously calculated information of cell density and cell morphology and simultaneously counted biomass information, the machine learning component 510 may determine the change, acceleration rate, transformation, or other indicators of cell bioactivity within the bioreactor. The predictive results from machine learning component 510 may include images or videos in which cell density is within an acceptable range, and/or cell morphology is normal or images or videos in which cell density falls outside of an acceptable range, such as being too high or too low, and/or cell morphology being abnormal, or the inference or diagnosis of a cause of the unacceptable cell density, and/or the abnormal cell morphology. For example, the machine learning component 510 may be trained to diagnose that a cause of a cell density being too low is insufficient culture or growth medium, insufficient oxygen concentration, inadequate stirring, and/or unhealthy cells. Using such a training mechanism, the machine learning component 510 may accurately inform the processors 320 and/or 420 which imaging and/or growth settings need to be adjusted. In such a manner, growth conditions may be dynamically adjusted within the bioreactor based on a current condition of the cells.

The machine learning component 510 may further be trained by a supervised feedback mechanism to account for additional user input from cell culture operators following an inference or a diagnosis. For example, if the additional user input indicates that an inference or a diagnosis by the machine learning component 510 is inaccurate or is only partially accurate, such additional user input may further train the machine learning component 510. In such a manner, the machine learning component 510 may continuously enhance an accuracy of its inferences or diagnoses.

Going back to the bioreactor as described with reference to FIGS. 1A and 1B, the base 100 may be made from materials with clear clarity such as glass, polystyrene, polymer such as polycarbonate, or Polyethylene Terephthalate (PET). In some embodiments, a volume of the bioreactor may be approximately 30 milliliters (mL). In some embodiments, a volume of the bioreactor may range from approximately 10 mL to 50 mL. In some embodiments, a volume of the bioreactor may raise up to approximately 150 mL where the lid may contain multiple Luer connecters 140. The lid 130 may be made from a gel resin. The membrane 120 may include polytetrafluoroethylene (PTFE) that is naturally and permanently hydrophobic and ideal for filtering gases or other similar polymers.

Figure 6:
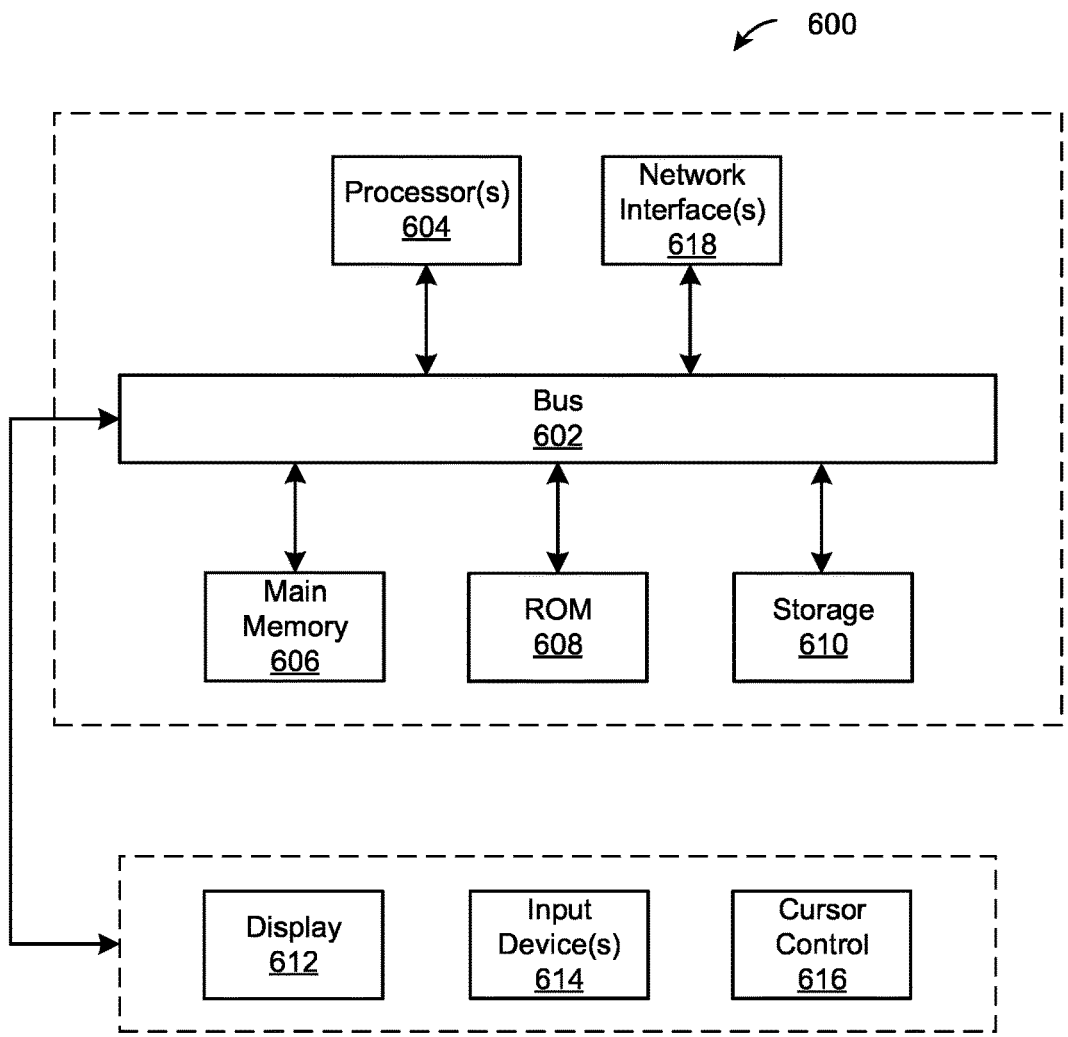
FIG. 6 is a schematic block diagram of a computer system upon which any of the embodiments described herein may be implemented.

FIG. 6 illustrates a block diagram of a computing system 600 upon which any of the embodiments described herein may be implemented. The computer system 600 includes a bus 602 or other communication mechanism for communicating information, one or more hardware processors 604 coupled with bus 602 for processing information. The hardware processors 604 may be implemented and deployed at edge side, for example, as any of the processors 510, 420, or 320. The computing system 600 also includes a main memory 606, such as a random-access memory (RAM), cache and/or other dynamic storage devices, coupled to bus 602 for storing information and instructions to be executed by processor 604. Main memory 606 also may be used for storing temporary variables or other intermediate information during execution of instructions to be executed by the hardware processors 604. Such instructions, when stored in storage media accessible to the hardware processors 604, render computer system 600 into a special-purpose machine that is customized to perform the operations specified in the instructions.

The computing system 600 further includes a read only memory (ROM) 608 or other static storage device coupled to bus 602 for storing static information and instructions for processor 604. A storage device 610, such as a magnetic disk, optical disk, or USB thumb drive (Flash drive), etc., is provided and coupled to bus 602 for storing information and instructions. The computing system 600 may be coupled via bus 602 to output device(s) 612, such as a cathode ray tube (CRT) or LCD display (or touch screen), for displaying information to a computer user who may be the cell culture operator or lab manager. Input device(s) 614 deployed at the cloud or remote ends outside the operating clean room, including alphanumeric and other keys, are coupled to bus 602 for remotely communicating information and command selections to the hardware processors 604. Another type of user input device is cursor control 616. The computing system 600 also includes an interactive human-machine or human-robot interface 618 coupled to bus 602.

Unless the context requires otherwise, throughout the present specification and claims, the word "comprise" and variations thereof, such as, "comprises" and "comprising" are to be construed in an open, inclusive sense, that is as "including, but not limited to." Recitation of numeric ranges of values throughout the specification is intended to serve as a shorthand notation of referring individually to each separate value falling within the range inclusive of the values defining the range, and each separate value is incorporated in the specification as it were individually recited herein. Additionally, the singular forms "a," "an" and "the" include plural referents unless the context clearly dictates otherwise. The phrases "at least one of," "at least one selected from the group of," or "at least one selected from the group consisting of," and the like are to be interpreted in the disjunctive (e.g., not to be interpreted as at least one of A and at least one of B).

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment but may be in some instances. Furthermore, the particular features, structures, or characteristics may be combined in any suitable manner in one or more embodiment. A component being implemented as another component may be construed as the component being operated in a same or similar manner as another component, and/or comprising same or similar features, characteristics, and parameters as another component.

What is claimed is:

1. A bioreactor configured to culture cells, the bioreactor comprising a bottom, side surfaces disposed above the bottom, and a lid disposed above the side surfaces, the side surfaces comprising:
    two opposing curved or convoluted surfaces;
    two opposing flat surfaces; and
    windows disposed on the respective flat surfaces, the windows having a higher degree of transparency compared to other portions of the bottom and the side surfaces, wherein images or videos of cells are captured through the windows by an imaging device placed against a window; and
    the lid comprising a connector attachable to an external device.

2. The bioreactor of claim 1, wherein the external device comprises a liquid handling or a stirring component, and an operation of the external device is controlled based on a density of the cells captured by the imaging device within the window, or a morphology of the cells captured within the window.

3. The bioreactor of claim 1, wherein the imaging device translates to capture images of additional bioreactors fixed onto the rotatable rack.

4. The bioreactor of claim 1, wherein the lid comprises a shaft.

5. The bioreactor of claim 4, wherein the shaft comprises a channel through which liquids are injected into or extracted from an interior region of the bottom.

6. The bioreactor of claim 5, wherein the shaft has a constant diameter throughout a length of the shaft.

7. The bioreactor of claim 1, wherein the bottom further comprises a circular periphery positioned at a proximal end of the bioreactor relative to the two opposing curved or convoluted surfaces and the two opposing flat surfaces.

8. The bioreactor of claim 7, wherein the lid comprises a shell fitting over the circular periphery of the bottom.

9. The bioreactor of claim 8, wherein the shell comprises an array of radially scattered air holes.

10. The bioreactor of claim 1, wherein the connector comprises a male Luer interface configured to mate with a female Luer interface of the external device, the external device comprising a liquid handling device, a harvesting device, or a stirring device.

11. The bioreactor of claim 1, wherein the external device comprises a liquid handling or a stirring component, and an operation of the external device is controlled based on a density of the cells captured by the imaging device within the window, or a morphology of the cells captured within the window.

12. A method of capturing images or videos of cells, the method comprising:
    culturing cells within a bioreactor, wherein the bioreactor comprises a bottom, side surfaces disposed above the bottom, and a lid disposed above the side surfaces, the side surfaces comprising:
        two opposing curved or convoluted surfaces;
        two opposing flat surfaces; and
        windows disposed on the respective flat surfaces, the windows having a higher degree of transparency compared to other portions of the bottom and the side surfaces;
    positioning an imaging device against a window of the windows; and
    capturing the images or the videos of the cells through the window.

13. The method of claim 12, wherein the lid comprises a connector attachable to an external device, and the method further comprises:
   determining a density of the cells captured by the imaging device within the window; and
   controlling an operation of the external device based on the density of the cells captured by the imaging device within the window.

14. The method of claim 13, wherein the external device comprises a stirrer, and the method further comprises:
   controlling a rotational speed or a duration of the stirrer based on the density of the cells within the bioreactor.

15. The method of claim 13, wherein the external device comprises a liquid injection device, and the method further comprises:
   controlling an amount of a growth medium to be injected into the bottom by the liquid injection device based on the density of the cells within the bioreactor.

16. The method of claim 13, wherein the external device comprises a liquid injection device, and the method further comprises:
   controlling an amount of a buffer to be injected into the base by the liquid injection device based on the density of the cells within the bioreactor.

17. The method of claim 13, wherein the lid comprises a connector attachable to an external device, and the method further comprises:
   determining a morphology of the cells captured by the imaging device within the window; and
   controlling an operation of the external device based on the morphology of the cells captured by the imaging device within the window.

18. The method of claim 17, wherein the external device comprises a stirrer, and the method further comprises:
   controlling a rotational speed or a duration of the stirrer based on the morphology of the cells within the bioreactor.

19. The method of claim 17, wherein the external device comprises a liquid injection device, and the method further comprises:
   controlling an amount of a growth medium to be injected into the bottom by the liquid injection device based on the morphology of the cells within the bioreactor.

20. The method of claim 17, wherein the external device comprises a liquid injection device, and the method further comprises:
   controlling an amount of a buffer to be injected into the base by the liquid injection device based on the morphology of the cells within the bioreactor.

* * * * *